United States Patent [19]
Karayiannis et al.

[11] Patent Number: 5,856,084
[45] Date of Patent: Jan. 5, 1999

[54] HEPATITIS B VACCINE

[75] Inventors: Peter Karayiannis; Howard Christopher Thomas, both of London, England

[73] Assignee: Imperial College of Science, Technology & Medicine, London, England

[21] Appl. No.: 500,914

[22] PCT Filed: Feb. 2, 1995

[86] PCT No.: PCT/GB95/00208

§ 371 Date: Dec. 28, 1995

§ 102(e) Date: Dec. 28, 1995

[87] PCT Pub. No.: WO95/21189

PCT Pub. Date: Aug. 10, 1995

[30] Foreign Application Priority Data

Feb. 2, 1994 [GB] United Kingdom .................. 9401987

[51] Int. Cl.$^6$ .......................... C07K 14/02; C07K 16/08; C12Q 1/70; G01N 33/53
[52] U.S. Cl. ................. 435/5; 435/7.1; 435/69.1; 435/69.3; 435/70.1; 435/189.1; 435/240.1; 435/320.1; 435/325.1; 435/975; 530/350; 530/388.3; 530/389.4; 530/806; 530/810; 530/826; 424/139.1; 424/189.1; 424/185.1; 424/193.1; 424/227.1
[58] Field of Search ................. 435/5, 7.1, 69.1, 435/189.1, 320.1, 240.1, 69.3, 70.1, 325.1, 975; 530/300, 350, 388.3, 389.4, 806, 826, 810; 536/23.72, 24.32; 424/139.1, 189.1, 185.1, 193.1, 227.1

[56] References Cited

U.S. PATENT DOCUMENTS 5,593,825  1/1997  Carman ........................................ 435/5
5,595,739  1/1997  Carman ................................. 435/189.1

FOREIGN PATENT DOCUMENTS 0 511 855   11/1992   European Pat. Off. .
WO 91/14703 10/1991   WIPO .
WO 94/26904 11/1994   WIPO .

*Primary Examiner*—Michael P. Woodward
*Assistant Examiner*—Mary K. Zeman
*Attorney, Agent, or Firm*—Nixon & Vanderhye

[57] ABSTRACT

A variant or so-called "escape mutant" HBsAg protein or fragment thereof displaying the antigenicity of hepatitis B virus surface antigen is disclosed, in which the mutant protein or fragment thereof (mHBsAg) comprises a modified 'a' determinant in which at least two amino acids are inserted downstream of position 122 of the wild type HBsAg sequence. A vaccine comprising the mHBsAg is provided, as is a kit for diagnostic in vitro detection of anti-mHBsAg antibodies and an antibody preparation comprising anti-mHBsAg antibodies.

20 Claims, 7 Drawing Sheets

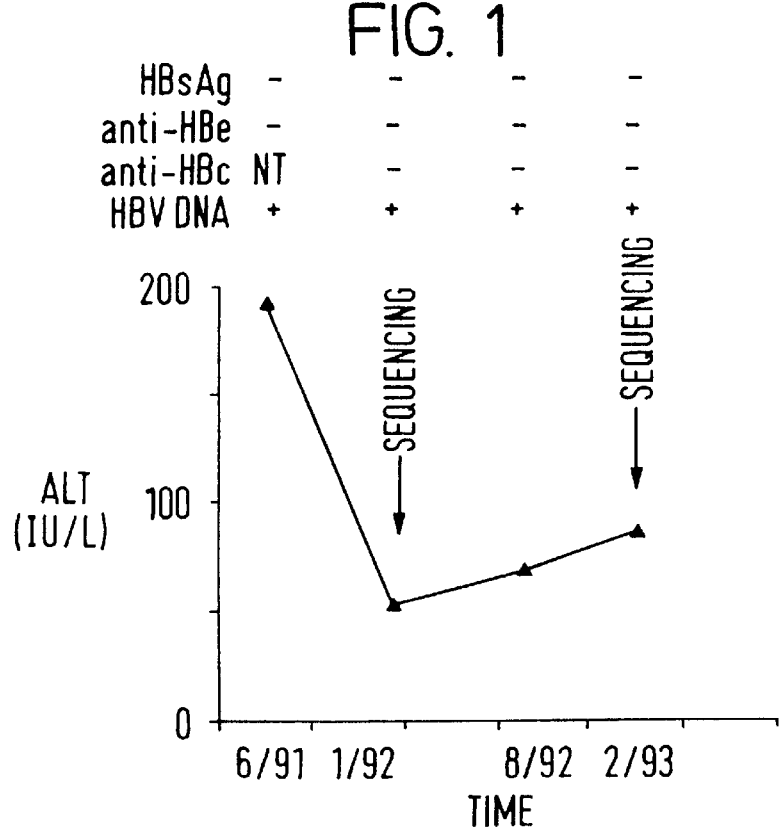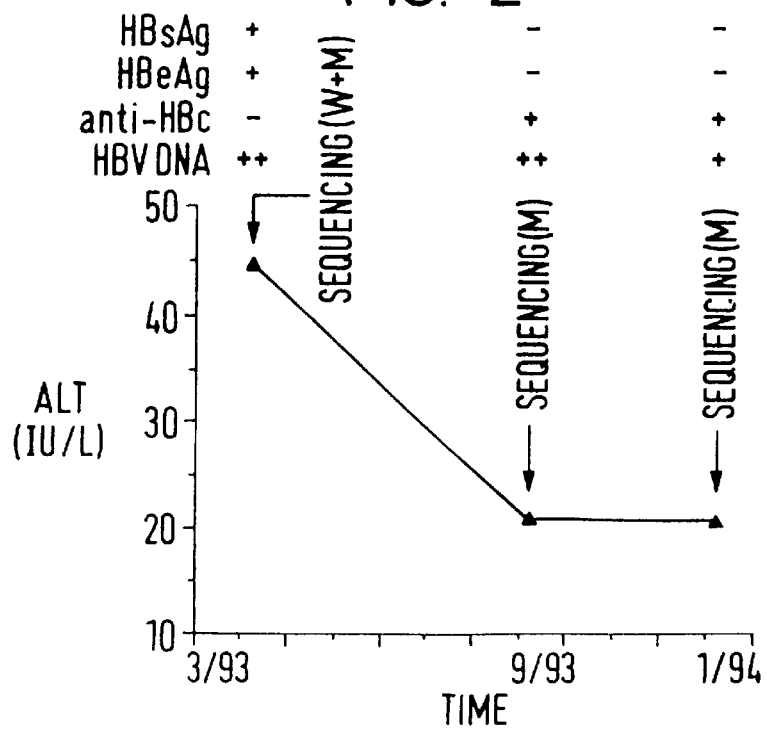

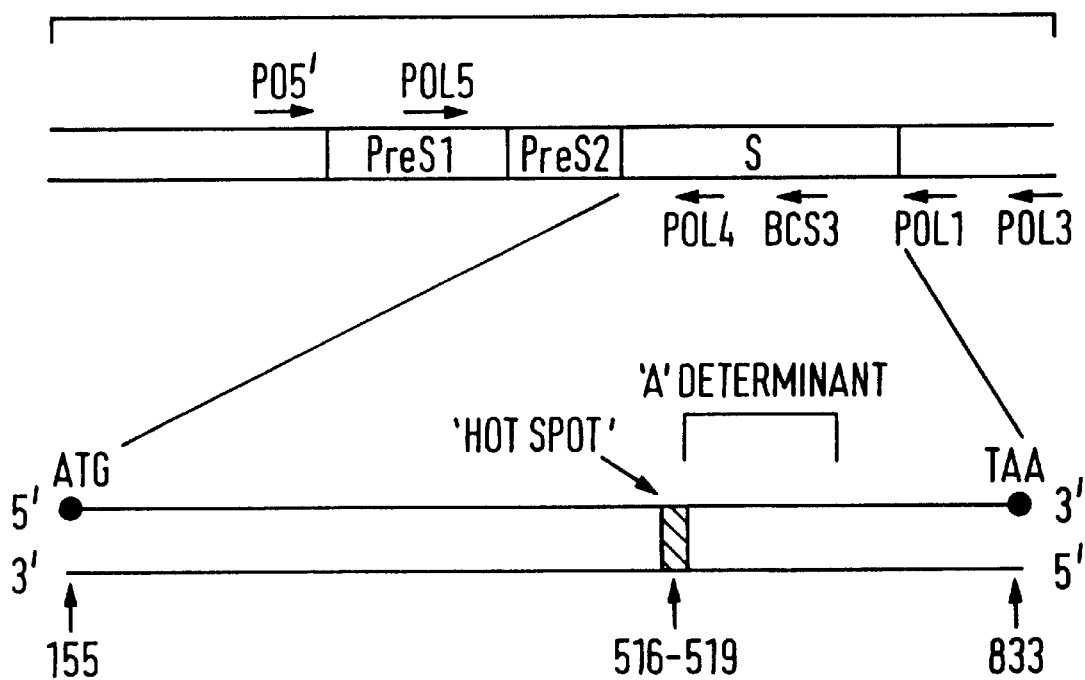

FIG. 5

|  | 514→ |  |  |  |  |  |  | 521→ |  |  |  |  | 532→ |  |
|---|---|---|---|---|---|---|---|---|---|---|---|---|---|---|
| WILD TYPE (adw) | T | G | C | A | A | A | A | C | C | T | G | C | A | C | A | A | C | T | C | C | T |
|  | 121 | | 122 | | | 123 | 124 | 125 | 126 | 127 |
|  | Cys | | Lys | | | Thr | Cys | Thr | Thr | Pro |
| MUTANT 1 | – | – | – | – | C | G | G | C | A | A | – | – | – | – | – | – | – | – | – | – | – |
|  | – | | – | | | Arg | Ala | | | | |
| MUTANT 2 | – | – | – | – | C | A | C | G | G | G | G | C | G | – | – | – | – | – | – | – | – |
|  | – | | – | | Thr | Arg | Gly | Ala | | | |

FIG. 6

```
             10         20         30         40         50         60
    ATGGAGAACATCACATCAGGACTCCTAGGACCCCTGCTCGTGTTACAGGCGGGGTTTTTC
    X:::::::::: ::::::::::::::::::::::::::::::::::::::::::::::::
    ATGGAGAACATCGCATCAGGACTCCTAGGACCCCTGCTCGTGTTACAGGCGGGGTTTTTC
           160        170        180        190        200        210
             70         80         90        100        110        120
    TTGTTGACAAAAATCCTCACAATACCACAGAGTCTAGACTCGTGGTGGACTTCTCTCAAT
    :::::::::: ::::::::::::::::::::::::::::::::::::::::::::::::
    TTGTTGACAAAAATCCTCACAATACCACAGAGTCTAGACTCGTGGTGGACTTCTCTCAAT
           220        230        240        250        260        270
            130        140        150        160        170        180
    TTTCTAGGGGAACACCCGTGTGTCTTGGCCAAAATTCGCAGTCCCAAATCTCCAGTCAC
    ::::::::::::::::::::::::::::::::::::::::::::::::::::::::::::
    TTTCTAGGGGAACACCCGTGTGTCTTGGCCAAAATTCGCAGTCCCAAATCTCCAGTCAC
           280        290        300        310        320        330
            190        200        210        220        230        240
    TCACCAACCTGTTGTCCTCCAATTTGTCCTGGTTATCGCTGGATGTGTCTGCGGCGTTTT
    :::::::: ::::::::: ::::::::::::::::::::::::::::::::::::::::
    TCACCAACTTGTTGTCCTCCGATTTGTCCTGGTTATCGCTGGATGTGTCTGCGGCGTTTT
           340        350        360        370        380        390
            250        260        270        280        290        300
    ATCATCTTCCTCTGCATCCTGCTGCTATGCCTCATCTTCTTGTTGGTTCTTCTGGACTAT
    ::::::::::::::::::::::::::::::::::::::::::::::::::::::::::::
    ATCATCTTCCTCTGCATCCTGCTGCTATGCCTCATCTTCTTGTTGGTTCTTCTGGACTAT
           400        410        420        430        440        450
            310        320        330        340        350        360
    CAAGGTATGTTGCCCGTTTGTCCTCTAATTCCAGGATCATCAACAACCAGCACCGGACCA
    :::::::::::::::::::::::::::::::::::::::::::::: :::::::::::::
    CAAGGTATGTTGCCCGTTTGTCCTCTAATTCCAGGATCATCAACCACCAGCACCGGACCA
           460        470        480        490        500        510
            370        380        390        400        410        420
    TGCAAACGGGCAACCTGCACAACTCCTGCTCAAGGAACCTCTATGTTTCCTCATGTTGC
    :::::X         :::::::::::::::::::::::::::::::::::::::::::::
    TGCAAA------ACCTGCACGACTCCTGCTCAAGGAACCTCTATGTTTCCTCATGTTGC
           520        530        540        550        560
            430        440        450        460        470        480
    TGTACAAAACCTACGGACGGAAACTGCACCTGTATTCCCATCCCATCATCTTGGCGTTTC
    ::::::::::::::::::::::::::::::::::::::::::::::::::::: ::::
    TGTACAAAACCTACGGACGGAAACTGCACCTGTATTCCCATCCCATCATCTTGGGCTTTC
    570        580        590        600        610        620
            490        500        510        520        530        540
    GCAAAATACCTATGGGAGTGGGCCTCAGTCCGTTTCTCTTGGCTCAGTTTACTAGTGCCA
    ::::::::::::::::::::::::::::::::::::::::::::::::::::::::::::
    GCAAAATACCTATGGGAGTGGGCCTCAGTCCGTTTCTCTTGGCTCAGTTTACTAGTGCCA
    630        640        650        660        670        680
            550        560        570        580        590        600
    TTTGTTCAGTGGTTCGTAGGGCTTTCCCCCACTGTCTGGCTTTCAGTTATATGGATGATG
    ::::::::::::::::::::::::::::::::::::::::::::::::::::::::::::
    TTTGTTCAGTGGTTCGTAGGGCTTTCCCCCACTGTCTGGCTTTCAGTTATATGGATGATG
    690        700        710        720        730        740
            610        620        630        640        650        660
    TGGTTTTGGGGGCCAAGTCTGATCAACATCTTGAGTCCCTTTATGCCGCTGTTACCAATT
    ::::::::::::::::::::::::  ::::::::::::::::::::::::::::::::::
    TGGTTTTGGGGGCCAAGTCTGTACAACATCTTGAGTCCCTTTATGCCGCTGTTACCAATT
    750        760        770        780        790        800
            670        680
    TTCTTTTGTCTTTGGGTATACATTTAA
    :::::::::::::::::::::::::::
    TTCTTTTGTCTTTGGGTATACATTTAA
    810        820        830
```

FIG. 7

```
         10        20        30        40        50        60
ATGGAGAACATCACATCAGGACTCCTAGGACCCCTGCTCGTGTTACAGGCGGGGTTTTC
X:::::::::: ::::::::::::::::::::::::::::::::::::::::::::::::
ATGGAGAACATCGCATCAGGACTCCTAGGACCCCTGCTCGTGTTACAGGCGGGGTTTTC
         10        20        30        40        50        60
         70        80        90       100       110       120
TTGTTGACAAAAATCCTCACAATACCACAGAGTCTAGACTCGTGGTGGACTTCTCTCAAT
::::::::::::::::::::::::::::::::::::::::::::::::::::::::::::
TTGTTGACAAAAATCCTCACAATACCACAGAGTCTAGACTCGTGGTGGACTTCTCTCAAT
         70        80        90       100       110       120
        130       140       150       160       170       180
TTTCTAGGGGAACACCCGTGTGTCTTGGCCAAAATTCGCAGTCCCAAATCTCCAGTCAC
::::::::::::::::::::::::::::::::::::::::::::::::::::::::::
TTTCTAGGGGAACACCCGTGTGTCTTGGCCAAAATTCGCAGTCCCAAATCTCCAGTCAC
        130       140       150       160       170       180
        190       200       210       220       230       240
TCACCAACCTGTTGTCCTCCAATTTGTCCTGGTTATCGCTGGATGTGTCTGCGGCGTTTT
:::::::: :::::::::::: :::::::::::::::::::::::::::::::::::::
TCACCAACTTGTTGTCCTCCGATTTGTCCTGGTTATCGCTGGATGTGTCTGCGGCGTTTT
        190       200       210       220       230       240
        250       260       270       280       290       300
ATCATCTTCCTCTGCATCCTGCTGCTATGCCTCATCTTCTTGTTGGTTCTTCTGGACTAT
::::::::::::::::::::::::::::::::::::::::::::::::::::::::::::
ATCATCTTCCTCTGCATCCTGCTGCTATGCCTCATCTTCTTGTTGGTTCTTCTGGACTAT
        250       260       270       280       290       300
        310       320       330       340       350       360
CAAGGTATGTTGCCCGTTTGTCCTCTAATTCCAGGATCATCAACAACCAGCACCGGACCA
:::::::::::::::::::::::::::::::::::::::::::: :::::::::::::::
CAAGGTATGTTGCCCGTTTGTCCTCTAATTCCAGGATCATCAACCACCAGCACCGGACCA
        310       320       330       340       350       360
        370       380       390       400       410       420
TGCAAAACACGGGGCGCCTGCACAACTCCTGCTCAAGGAACCTCTATGTTTCCTCATGT
:::::::        ::::::: :::::::::::::::::::::::::::::::::::
TGCAAAA---------CCTGCACGACTCCTGCTCAAGGAACCTCTATGTTTCCTCATGT
               370       380       390       400       410
        430       440       450       460       470       480
TGCTGTACAAAACCTACGGACGGAAACTGCACCTGTATTCCCATCCCATCATCTTGGGCT
::::::::::::::::::::::::::::::::::::::::::::::::::::::::::::
TGCTGTACAAAACCTACGGACGGAAACTGCACCTGTATTCCCATCCCATCATCTTGGGCT
        420       430       440       450       460       470
        490       500       510       520       530       540
TTCGCAAAATACCTATGGGAGTGGGCCTCAGTCCGTTTCTCTTGGCTCAGTTTACTAGTG
::::::::::::::::::::::::::::::::::::::::::::::::::::::::::::
TTCGCAAAATACCTATGGGAGTGGGCCTCAGTCCGTTTCTCTTGGCTCAGTTTACTAGTG
        480       490       500       510       520       530
        550       560       570       580       590       600
CCATTTGTTCAGTGGTTCGTAGGGCTTTCCCCCACTGTCTGGCTTTCAGTTATATGGATG
::::::::::::::::::::::::::::::::::::::::::::::::::::::::::::
CCATTTGTTCAGTGGTTCGTAGGGCTTTCCCCCACTGTCTGGCTTTCAGTTATATGGATG
        540       550       560       570       580       590
        610       620       630       640       650       660
ATGTGGTTTTGGGGCCAAGTCTGTACAACATCTTGAGTCCCTTTATGCCGCTGTTACCA
::::::::::::::::::::::::::::::::::::::::::::::::::::::::::
ATGTGGTTTTGGGGCCAAGTCTGTACAACATCTTGAGTCCCTTTATGCCGCTGTTACCA
        600       610       620       630       640       650
        670       680       690
ATTTTCTTTTGTCTTTGGGTATACATTTAA
::::::::::::::::::::::^:::::::V
ATTTTCTTTTGTCTTTGGGTATACATTTAA
        660       670       680
```

FIG. 8

| DESIGNATION | | SEQUENCES | NUCLEOTIDE POSITION |
|---|---|---|---|
| Pre-S1 | P05¹ ANTISENSE | 5'-TGCGGGTCACCATAT | (2818-2833) |
| Pre-S2 | POL5 ANTISENSE | 5'-CAATCGGCAGTCAGG | (3125-3139) |
| S | POL4 SENSE | 5'-AGGCATAGCAGCAGG | (428-414) |
|  | BCS3 SENSE | 5'-GGCACTAGTAAACTGAGCCA | (687-660)¹ |
|  | POL1 SENSE | 5'-GCAAAGTTCCCCAACTTC | (912-895) |
|  | POL3 SENSE | 5'-AAGGATCCAGTTGGC | (1409-1395) |

¹CARMAN et al., 1990

FIG. 9

|  | DATE | RFHBs1 | RFHBs2 | RFHBs7 | AusRIA |
|---|---|---|---|---|---|
| PATIENT 1 | FEBRUARY 1993 | -¹ | - | - | - |
| PATIENT 2 | SEPTEMBER 1993 | 31 | 23 | 2 | - |
| CONTROL |  | 19 | 176 | 3 | 74 |

1 NEGATIVE

FIG. 10

|  | WILD TYPE adw | | CHINESE adw | |
|---|---|---|---|---|
|  | nt% | aa% | nt% | aa% |
| ISOLATE 1 | 94.0 | 91.2 | 93.7 | 90.8 |
| ISOLATE 2 | 93.6 | 90.8 | 93.3 | 90.4 |

HEPATITIS B VACCINE

FIELD OF THE INVENTION

This invention relates to recombinant DNA molecules which code for polypeptides having specificity towards a hepatitis B viral antigen.

More particularly this invention relates to a vaccine composition for stimulating the production of antibodies in humans to a variant hepatitis B virus.

BACKGROUND OF THE INVENTION

The cloning of the genomes of hepatitis B virions of different serotypes is well known in the art (Miller et al). Dane particles which are hepatitis B virions and are isolatable from infected patients have a diameter of approximately 42 nm. Each consists of an envelope comprising the hepatitis B surface antigen (HBsAg), a capsid (HBcAg), an endogenous polymerase and a DNA genome. A third polypeptide, 'e' antigen (HBeAg) is made by the hepatitis B virus and found in solubilized form in serum.

Infection with hepatitis B virus (HBV) is a serious, widespread problem but vaccines for use in mass immunisation are now widely available. Vaccines commercially available against HBV comprise hepatitis B virus surface antigen (HBsAg) either in native or recombinant form. The authentic (or wild type) hepatitis B virus surface antigen can be recovered from plasma of infected individuals as a particle of about 22 nm comprising of two proteins known as P24 and its glycosylated derivative GP28, both of which are encoded by a 226 amino acid coding sequence on the HBV genome known as the S protein coding sequence or HBV S-gene (Tiollais et al., (1985)). The complete amino acid sequence as well as the nucleotide sequence encoding, HBsAg is given in Valenzuela et al., *Nature* 280 815 (1979) (SEQ ID NO:1). The numbering system used by Tiollais et al. to define nucleotide and amino acid positions is used herein.

Insertion of HBV S-gene coding sequences under the control of yeast promoters on expression vectors to enable expression of HBsAg in *S. cerevisiae* for vaccine production has been described by Harford et al. in *Develop. Biol. Standard* 54 125 (1983), Valenzuela et al., *Nature* 298 347 (1982) and Bitter et al., *J. Med. Virol.* 25 123 (1988). Expression in Pichia pastoris has been described by Gregg et al., *Biotechnology* 5 479 (1987), (see also European Patent Publication No. 0226846) as has expression in *Hansenula polymorpha* (European Publication No. 0299108).

Vaccines have also been prepared from hybrid immunogenic particles comprising HBsAg protein as described in European Patent Publication No. 0278940. Such immunogenic particles can contain, for example, all or parts of the HBsAg precursor protein encoded by the coding sequence which immediately precedes the HBV-S gene on the HBV genome, referred to herein as the Pre-S coding sequence. The Pre-S coding sequence normally codes for 163 amino acids (in the case of the ay HBV sub type) and comprises a Pre-S1 coding sequence and a Pre-S2 coding sequence. The latter codes for 55 amino acids and immediately precedes the S protein coding sequence (European Publication No. EP-A-0278940).

The surface antigen (the S antigen) open reading frame of HBV-DNA is divided into three regions, pre-S1, pre S-2 and S. It encodes three envelope proteins of HBV termed: large, middle and major proteins. The major protein, HBsAg, consists of 226 amino acids and is encoded by the S gene (Tiollais et al., (1981); Tiollais et al., (1987) and Lau et al.). All three envelope proteins contain HBsAg antigenic sites and are easily detected by conventional immunoassays for HBsAg. These immunoassays are extensively used for diagnosing HBV infection and screening blood donors worldwide. The HBsAg reactivity is dependent on the structural conformation of the hydrophilic region from amino acids 124–147 which is defined as the 'a' determinant (Ashton-Rickardt et al. and Brown et al.). This is common to all HBV subtypes and antibody to it confers protection against reinfection with any of the subtypes.

HBV-DNA sequences hybridising under highly stringent conditions with an HBV probe have been shown in the liver, serum and blood mononuclear cells of subjects negative for serum HBsAg (Brechot et al. (1985) and Thier et al). Recent results from different laboratories using dot blot hybridisation or Polymerase Chain Reaction (PCR) confirm the presence of HBV DNA sequences in serum from HBsAg negative subjects. The development of PCR techniques has permitted the detection of very low levels of HBV replication in many patients and has allowed sequencing of many isolates which have identified genetic variation in some isolates of the virus (Carman et al., (1990); Brechot et al., (1991); Blum et al.). In Taiwan and Sardinia, where HBV is highly endemic, 1.7% and 0.3% of HBsAg negative healthy blood donors had HBV DNA in their sera detectable by dot blot hybridisation (Lai et al., (1989) and Sun et al.) In mainland China, a molecular epidemiological investigation using PCR in anti-HB-positive individuals indicated the existence of HBV carriers with undetectable HBsAg, which accounts for 3% of the Chinese general population (Luo et al.)

Antigenic subtypes of HBV are defined serologically and have been shown to be caused by a single base changes in the region of the genome encoding HBsAg (Okamoto et al.). However, all presently known antigenic subtypes contain the 'a' determinant consisting of amino acids 124 to 147 of HBsAg. Antibodies to the 'a' determinant confers protection against all subtypes. It has been shown by in vitro mutagenesis that the cysteine at position 147 and the proline at position 142 are important for the exhibition of full antigenicity of the 'a' determinant (Ashton-Rickardt et al.).

Additionally, Howard Thomas and William Carman, detailed in WO 91/14703 a variant of an HBsAg fragment in a vaccinated child born to an HBV infected mother. Sequencing revealed a point mutation from guanosine to adenosine at nucleotide position 587 resulting in an amino acid change from glycine to arginine at position 145 in the 'a' determinant of HBsAg (see also Carman et al., (1990)). Similar HBV mutants have been reported to replicate in the host under humoral immune pressure, either actively (vaccine) or passively (hyperimmune globulin) induced (Okamoto et al., (1992) and McMahon et al.) However, the persistent presence of both HBsAg and anti-HBs (vaccine induced) detected by conventional immunoassays, in the serum of some of these patients, suggests that the mutation does not result in complete loss of antigenicity (Carman et al., (1990), Okamoto et al., (1992) and McMahon et al.).

From the clinical and epidemiological view, it is more important to investigate the molecular features of HBV from subjects without any HBsAg reacting in standard assays. Sequencing results from a Japanese patient who was HBeAg and HBV-DNA, as well as anti-HBs positive showed that amino acids 9 to 22 of the pre-S2 region were deleted whereas amino acids at position 3 and 8 of the pre-S2, and 126, 131 and 133 of the first loop of the 'a' determinant of HBs were substituted (Moriyama et al.). Analysis of the deduced amino acid sequence from another isolate revealed substitutions at positions 3, 53 and 210 of the major HBs protein, all of which are outside the common 'a' determinant and cannot really explain the absence of HBsAg in serum (Liang et al.).

During the last decade, several putative variants or mutants of hepatitis B virus have been described. For instance, McMahon et al. have described a substitution of arginine for glycine in a putative monoclonal antibody binding domain of HBsAg (as deduced by DNA sequence analysis) in a liver transplant patient treated with anti-HBsAg monoclonal antibody (Cold Spring Harbor Symposium on the Molecular Biology of Hepatitis B Viruses, September, 1989).

In an investigation by Carman et al. and the subject of patent application WO 94/26904, a mutant hepatitis B virus having a modified 'a' determinant wherein two specific amino acids, asparagine and threonine, were inserted at position 122 of the HBsAg sequence. Further, a mutation at position 145, substituting glycine for the wild type arginine was also detailed in the amino acid sequence listing.

In another report, children and adults were found with circulating hepatitis B surface antigen, indicating viral replication, despite the presence of specific antibody (anti-HBs) after immunisation with one of two licensed hepatitis B vaccines (Zanetti et al.). Analysis of the HBsAg with monoclonal antibodies revealed that the circulating antigen did not carry the 'a' determinant or that this determinant was masked. It was concluded that emergence of a variant of hepatitis B virus had been detected, possibly due to epidemiological pressure associated with immunisation in an endemic area of infection. The variant was, however, not characterised further.

From the work of Zanetti et al. it is clear that a great disadvantage with presently available hepatitis B vaccines is that they may, at least in a host with a predisposing immunogenetic make-up, cause the appearance of an 'escape mutant', i.e. a replicating infectious virus that has mutated away from neutralising immunity. Such a variant virus obviously has the capacity to cause disease and may be assumed to be transmissible. The variant virus may therefore give rise to a serious immunisation problem since it is not effectively neutralised by antibodies produced by vaccines based on normal HBsAg. Other mutations have been described in HBV, but their significance in terms of altered antigenicity is unclear (Moriyama et al. and Lai et al., (1990)).

SUMMARY OF THE INVENTION

In China, a highly endemic area for HBV infection, recent studies, utilising PCR, suggest that 30–40% of HBsAg negative patients with either cryptogenic cirrhosis, chronic active hepatitis (CAH) or chronic persistent hepatitis (CPH), have replicating HBV-DNA in serum or liver tissue (Zhang et al.). These studies show, that a variant of HBV exists in the Chinese population, characterised by undetectable HBsAg in serum. Surprisingly, such a putative mutant has never been characterised at the molecular level.

The isolates from our Chinese patients (i.e. patients without any detectable HBsAg) are insertion mutants where additional amino acids are inserted between codons 122 and 124, immediately before the 'a' determinant. This sequence variation has not previously been described in any known HBV subtype and was not seen in 30 HBsAg positive Chinese patients from the same region. It is interesting to note that the region in which the insertion occurred is an important epitope area of HBsAg. The inserted sequence is found immediately downstream of codon 122 which determines the subtype determinant (d) and immediately upstream of the 'a' determinant. All nucleotide and amino acid sequences before and after codon position 122 are as detailed in wild type HBV (FIGS. 6 and 7). Without wishing to be bound by theory, we believe this mutation results in a conformational change affecting epitopes of the 'a' determinant and of the 'd' subtype. One likely possibility is that the insertion of the amino acids changes the epitopes by affecting the spatial organisation of the two loops of the 'a' determinant. Another possibility is that the first loop of the 'a' determinant, defined by monoclonal antibodies (Waters et al.), may include more upstream amino acids (than previously thought). We propose that these amino acids are being formed by a disulphide bridge upstream of 122 rather than 124 as previously suggested (Waters et al. and Ashton-Rickardt et al.). The inserted amino acids would increase the span of the loop from 14 to 16 or 17 amino acids therefore altering the conformation of this loop, preventing binding of neutralising antibody.

In this invention, we describe a new variant or 'escape mutant' of HBV isolated from Chinese patients whose serum was positive for HBV-DNA by dot blot hybridisation but HBsAg negative by commercial polyclonal antibody based immunoassays. Additionally, the present invention overcomes, or at least mitigates, the disadvantages associated with known HBV vaccines as these vaccines are ineffective for these newly discovered mutants.

The present invention provides characterisation of newly ascertained mutants of HBV that have at least two amino acid insertions immediately downstream of position 122 at the HBV envelope region. The present invention provides methods for determining the presence of the mutant HBV in a test sample, and reagents useful in these methods. All aspects of this invention provide a modification of the 'a' determinant in which there is an insertion of at least two amino acids downstream of position 122 of the HBsAg sequence, which corresponds to at least a six nucleotide insertion downstream of nucleotide 519 of the HBsAg genome.

The nucleic acid sequence derived from mutant HBV, or a portion thereof are useful as probes to determine the presence of mutant HBV in test samples. The sequence also makes available polypeptide sequences of mutant HBV antigen(s) encoded within the genome(s) of such mutant HBV and permits the production of polypeptides which are useful as standards or reagent sin diagnostic tests and/or as components of vaccines. Monoclonal and polyclonal antibodies directed against an epitope contained within these polypeptide sequences, also are useful for diagnostic tests as well as therapeutic agents, for screening of antiviral agents, and for the isolation of the mutant HBV from which these nucleic acid sequences are derived.

It is to be understood that this mutant HBsAg may also include Pre-S sequences if so desired.

The variant HBsAg protein or fragment thereof according to the invention is hereinafter abbreviated "mHBsAg".

It will be appreciated that these mHBsAg mutants are not in a 'naturally occurring' form but are synthetic or a highly purified material, free of blood products.

Preferably these mutants as described in the invention correspond to full length HBsAg and are identical to wild type HBsAg except for the insertion of at least two amino acid residues downstream of position 122.

Preferably the HBsAg mutants are in a highly purified form, for example in a state of purity greater than 75%, more preferably greater than 90%, and most preferably 95–100% pure.

In a further aspect of the present invention there is provided a vaccine composition comprising an immunoprotective amount of these HBsAg "escape mutants" combined with a suitable carrier.

Other aspects of the invention are described hereinbelow.

The mHBsAg and vaccine of the invention may be used to overcome the problems perceived by the emergence of an 'escape mutant' as defined hereinabove in which the area immediately upstream of 'a' determinant (the envelope region) of the viral HBsAg has undergone modification. In particular, the vaccine of the invention has the advantage in that it may be used to protect against, and prevent the emergence or transmission of, a variant HBV which is defined herein as having a modified HBV envelope region in the HBsAg amino acid sequence wherein there are at least two amino acids inserted downstream of position 122.

Accordingly there is also provided a method for protecting a human against disease symptoms associated with infection with said variant HBV, which method comprises administering to the human a safe and effective amount of the vaccine according to the invention.

In another aspect the present invention provides mHBsAg for use in therapy, especially prophylaxis.

The invention also provides the use of mHBsAg in the manufacture of a vaccine composition for protecting a human against disease symptoms associated with said variant HBV infection.

When used to immunise humans against an existing variant HBV virus it will be appreciated that the mHBsAg sequence in the vaccine will normally match, or be antigenically equivalent to, the mHBsAg sequence in the variant HBV virus.

Preferably the amino acid residues inserted after position 122 in the mHBsAg of the invention is such that it may be derived by an insertion of six or more nucleotides. The inserted nucleotides encoding the extra amino acids may affect any of the 3 nucleotides of codon 123 in normal HBsAg.

Theoretically, any mutation which changes the hydrophilicity of the envelope proteins can result in altering antigenicity and the appearance of variant HBV. The hydrophilicity of the wild type and that of the mutant in this region are quite different. A reduction in hydrophilicity described here is often correlated with a loss of antigenicity. The increased hydrophobicity of the mutant in the first loop may also result in an altered protein of the major protein in the lipid of the envelope thereby having a profound effect on the conformation.

In a preferred embodiment of the invention, the residues after position 122 of normal HBsAg may reduce the hydrophilicity of the 'a' determinant.

In another preferred embodiment of the invention the mHBsAg is identical to normal (wild type) HBsAg S-protein except for the insertion of at least two amino acid residues downstream of position 122.

In a particularly preferred embodiment of the invention the modification downstream of position 122, is an insertion of arginine and then alanine, respectively. Also preferably, an insertion downstream of position 122 of arginine, glycine and alanine in that order may be inserted.

Preferred features of each aspect of the invention are as for each other aspect, mutatis mutandis.

BRIEF DESCRIPTION OF THE DRAWINGS

FIG. 1 illustrates serial serum aminotransferase (ALT) levels from Patient No. 1. Normal levels are below 40 i*u*/L. Serum HBV markers were measured at various prints in time. In August 1992 HBV DNA was found by PCR yet HBsAg and the other HBV markers were undetected.

FIG. 2 illustrates serial serum ALT levels from Patient No. 2 as well as serum hepatitis B virus markers. Abbreviations indicate: w, wild type; m, mutant.

FIG. 3 is a diagrammatic representation of the surface gene open reading frame, position of the PCR and sequencing primers, and the overlapping polymerase open reading frame (P ORF). Shaded circles represent initiation and stop codons, whereas the shaded box indicates the insertion hot spot in relation to the 'a' determinant (positions 522–593). The nucleotide numbering is from a hypothetical EcoRI site as in published HBV DNA sequences, because the present isolates did not possess an EcoRI site.

FIG. 5 illustrates the nucleotide and amino acid sequences of Isolates 1 and 2 compared with wild type (adw) (SEQ ID NOS:6 & 7). The inserted sequences are underlined.

FIG. 6 illustrates the complete nucleotide sequence of mHBsAg Isolate 1(SEQ ID NOS:8 & 9). The top sequence represents that of the surface gene and 'a' determinant the mutant HBsAg isolate whereas the bottom sequence represents the wild type sequence. (- - -) represent points of amino acid insertion.

FIG. 7 illustrates the complete nucleotide sequence of mHBsAg Isolate 2. The top sequence represents that of the surface gene and 'a' determinant the mutant HBsAg isolate whereas the bottom sequence represents the wild type sequence. (- - -) represent points of amino acid insertion.

FIG. 8 depicts the synthetic oligonucleotide primers (SEQ ID NOS:10–15, respectively) used for the Polymerase Chain and sequencing reactions.

FIG. 9 illustrates positive/negative binding ratios of serum HBsAg from Patient Nos. 1 and 2 to monoclonal antibodies with adw wild type used as a control.

FIG. 10 sets out the nucleotide and amino acid sequence homologies of mutant S genes compared with previous published wild type sequence (adw) and a Chinese isolate from the same region as the wild type.

DETAILED DESCRIPTION OF THE INVENTION

Figure 4:
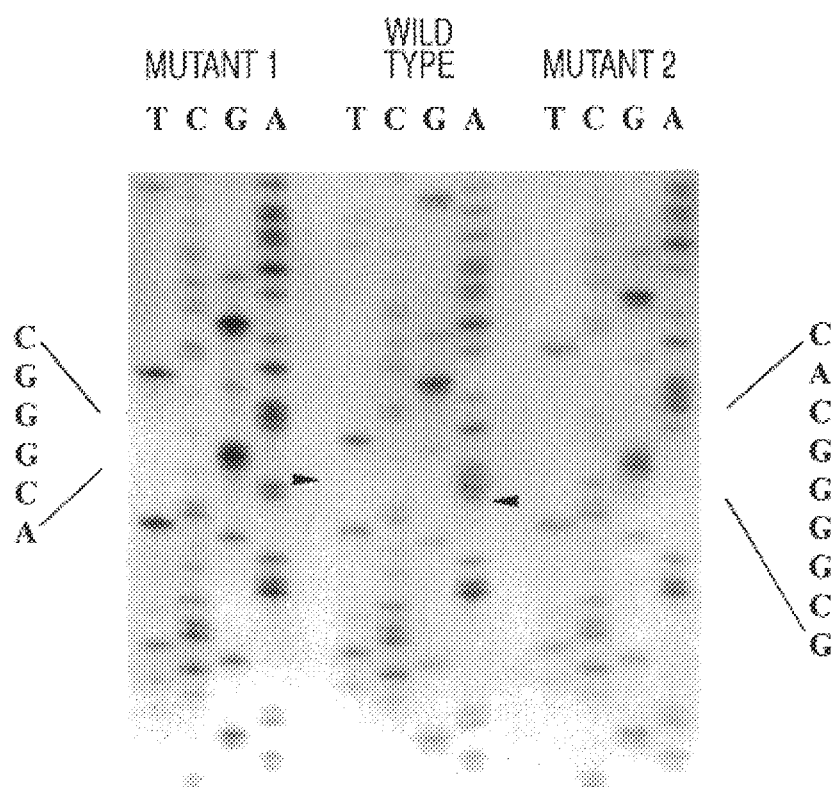
FIG. 4 is an autoradiograph showing the nucleotide insertion in Isolates 1 and 2 (left and right) compared with the wild type (centre) following direct sequencing of PCR products. The arrows indicate the point of insertion.

HBV mutations are more commonly found in particular areas of the sequence characterised by runs of bases. In the case under study the insertion is associated with a run of four adenines. This area is seemingly a "hot spot" for insertion in some isolates from Chinese HBsAG negative HBV carriers.

In a further aspect of the invention there is provided a process for preparing the mHBsAg and the vaccine composition obtained therefrom.

Preferably the mHBsAg is obtained synthetically, either by peptide synthesis or more preferably by recombinant DNA techniques.

Methods for the construction, manipulation and verification of recombinant DNA molecules and sequences are well known in the art. To modify the HBV S protein of HBsAg and obtain the mHBsAgs of the invention it is desirable to insert the codons CGG and GCA, or any other triplet codon combination which encodes arginine and alanine, respectively, downstream of position 122. Alternatively, codons CAC, GGG or GCG, or any other triplet codon combination encoding arginine, glycine and alanine, respectively, may be inserted between nucleotide positions 122 and 124.

Several methods are available to effect the appropriate change of sequence. One suitable method is complete de novo synthesis, by phosphite or phorphoramidite chemistry, of the desired coding sequence using viral or yeast codon frequencies.

Synthesis of DNA is available from several companies on a commercial basis. An example of such gene synthesis is described by Hayden and Mandecki, DNA 7: 571 (1988) and references therein.

A second method is to clone on a single strand vector an appropriate restriction fragment from a vector which already comprises the HBV genome and thereafter effect site specific in vitro mutagenesis as described by Botstein and Shortle, *Science* 229 1193 (1982). A culture of *E. coli* K12 strain C600 containing the recombinant plasmid pRIT10601 comprising an HBV genome of ay subtype cloned on pBR322 was deposited in accordance with the Budapest Treaty in the American Type Culture Collection on 2 Jun. 1982 under Accession Number ATCC 39132. The sequence coding for the S-gene specifying the 226 amino acid HBsAg protein or longer sequences coding for Pre S polypeptides can be excised from such clones by standard recombinant DNA techniques.

One appropriate restriction fragment is the 575 bp XbaI-AccI fragment from within the S-gene coding region of pRIT10601. Vector systems useful for in vitro mutagenesis are commercially available. The mutated gene fragment so obtained is reinserted into the S-gene.

A third method is to effect the desired mutational change using polymerase chain reaction (PCR) technology as described by Ho et al., *Gene* 77 51 (1989).

In each case the mHBsAg coding sequence may be expressed under the control of a suitable promoter in any suitable host.

Expression vectors comprising the DNA sequence encoding mHBsAg are novel and form a further aspect of the present invention. Hosts transformed with the said expression vectors form yet another aspect of the invention.

In a preferred aspect *S. cerevisiae, Pichia pastoris* or *Hansenula polymorpha* may be used as the host and expression is under the control of a yeast promoter, such as the yeast TDH3 promoter (glyceraldehyde-3-phosphate dehydrogenase gene, see Valenzuela et al., 1982; Bitter et al., 1988) or PH05 (Miyanohara et al., 1983), MOX, FMDH (see EP-A-0299108) and AOX (see EP-A-0226846).

The transformed host can be cultured or fermented by conventional means and the mHBsAg extracted and purified. Purification of HBsAg from yeast cells is well known in the art and can be done according to any of U.S. Pat. Nos. 4,649,192; 4,683,294; 4,694,074 or 4,738,926. Purification of the mHBsAg of the invention is carried out in an analogous manner.

Vaccines containing the mHBsAg are prepared by conventional techniques and will contain an immunoprotective amount of the mHBsAg preferably in buffered physiological saline and admixed or adsorbed with any of the various known adjuvants including aluminium hydroxide and aluminium phosphate. By "immunoprotective" is meant that enough of the mHBsAg is administered to elicit a sufficient protective antibody or cell mediated immune response to confer protection against the infectious agent without serious side effects. The amount of mHBsAg to be administered will depend on whether the vaccine is adjuvated and will generally comprise between 1 to 1000 mcg of protein.

Preferably 1 to 200 mcg protein is used or, more preferably 5 to 40 mcg protein. The amount and number of doses to be administered can be determined in standard dose range studies involving observation of antibody titres and other responses in subjects.

The mHBsAg may also be mixed with other HBsAg such as normal HBsAg or homogenous or composite HBsAg particles containing all or part or parts of the PreS1 or PreS2 polypeptides for vaccine formulation. It may also be mixed with hybrid HBsAg particles carrying epitopes from proteins from other organisms and with other immunogens to form bivalent or multivalent vaccines. Vaccine preparation is generally described in "Vaccines", edited by Voller et al., University Park Press, Baltimore, Md., U.S.A., 1978.

The mHBsAg is useful for inclusion as an immunological reagent in detection kits for variant HBV virus infection and the like. It can also be used to raise polyclonal and monoclonal antibodies by known methods, some of which monoclonal antibodies may be specific for the variant antigen and not recognise normal HBsAg.

In another embodiment of the invention polypeptides which react immunologically with serum containing mutant HBV antibodies and composites thereof, and the antibodies raised against the mutant HBV specific epitopes in these polypeptides are useful in immunoassays to detect the presence of mutant HBV antibodies, or the presence of the virus and/or viral antigens in biological test samples. The design of these immunoassays is subject to variation, and a variety of these are known in the art; a variety of these have been described herein. The immunoassay may utilise one viral antigen, such as a polypeptide derived from any clone-containing mutant HBV nucleic acid sequence, or from the composite nucleic acid sequences derived from the mutant HBV nucleic acid sequences in these clones, or from the mutant HBV genome from which the nucleic acid sequences in these clones is derived. Or, the immunoassay may use a combination of viral antigens derived from these sources. It may use, for example, a monoclonal antibody directed against the same viral antigen, or polyclonal antibodies directed against different viral antigens. Assays can include but are not limited to those based on competition, direct reaction or sandwich-type assays. Assays may use solid phases or may be performed by immunoprecipitation or any other methods which do not utilise solid phases. Examples of assays which utilise labels as the signal generating compound and those labels are described herein. Signals also may be amplified by using biotin and avidin, enzyme labels or biotin anti-biotin systems, such as that described in pending U.S. patent application Ser. Nos. 608,849; 070,647; 418,981; and 687,785. Recombinant polypeptides which include epitopes from immunodominant regions of mutant HBV may be useful for the detection of viral antibodies in biological test samples of infected individuals. It also is contemplated that antibodies may be useful in discriminating acute from non-acute infections. Kits suitable for immunodiagnosis and containing the appropriate reagents are constructed by packaging the appropriate materials, including the polypeptides of the invention containing mutant HBV epitopes or antibodies directed against mutant HBV epitopes in suitable containers, along with the remaining reagents and materials required for the conduct of the assay, as well as suitable assay instructions.

Accordingly in a preferred aspect of the invention there is provided a kit for the diagnostic in vitro detection of anti-mHBsAg antibodies in a biological medium, and in particular neutralising antibodies following vaccination, characterised in that it comprises:

a) mHBsAg as herein defined; and b) means adapted to detect the antigen-antibody reaction.

In a further aspect the invention provides an antibody preparation comprising anti-mHBsAg antibodies for use in the diagnosis, prevention or treatment of hepatitis B infection in humans. There is also provided a method of treating humans with an effective amount of such anti-mHBsAg antibody to prevent or treat hepatitis B infection.

The invention will now be illustrated by the following example.

EXAMPLE

Patient No. 1 was a 58 year old male, with a 6 year history of non-A, non-B chronic hepatitis. In August 1992, HBV-DNA was found by PCR in the absence of HBsAg and other HBV markers (FIG. 1). At this stage, the patient had cirrhosis.

Patient No. 2 was a 23 year old woman from the south of China, who on routine testing in March 1993 had a slightly elevated serum aminotransferase (ALT) level and was positive for HBsAg and HBeAg, but negative for both immunoglobulin (Ig)M and IgG anti-HBs. On follow-up in January 1994, she continued to be HBV-DNA positive and was now also anti-HB positive but negative for HBsAg, HBeAg and anti-HBs (FIG. 2)

Both patients were negative for hepatitis C virus (HCV) and HCV-RNA. Thirty HBsAg positive Chinese patients with chronic liver disease or hepatocellular carcinoma were studied from the same region.

Serological Investigation

HBsAg, HBeAg, total anti-HBc, IgM anti-HBs and anti-HBs were tested by commercially available enzyme immunoassays (Abbott Laboratories, North Chicago, Ill., U.S.A.). HBsAg and anti-HBs results were confirmed in the United Kingdom.

Monoclonal Antibody Binding

A panel of anti-HBs monoclonal antibodies known to bind to the 'a' determinant, were used to define more specifically changes in the 'a' determinant epitopes. Polystyrene beads (Northumbria Biologicals, Northumberland, UK) were coated with antibodies RFHBs-1, RFHBs-2 and RFHBs-7, and then incubated with the serum samples diluted 1:2 in 50% newborn-calf serum in phosphate-buffered saline, pH 7.2. Bound HBsAg was detected with $^{125}$I-anti-HBs from an 'AusRIA II' kit (Abbott Diagnostics), RFHBs-1 and RFHBs-2 bind to a cyclical peptide containing the sequence amino acids 124–137 and RFHBs-7 to a cyclical peptide from amino-acids 139–147 of HBsAg.

Hepatitis Markers

HBsAg, HBeAg, total anti-HBC, IgM anti-HBc, and anti-HBs were tested by enzyme immunoassay (Abbott Laboratories, North Chicago, Ill.).

Dot Blot Hybridisation

HBV-DNA was detected by dot blot hybridisation using a modification of a method detailed in Weller et al *J. Med. Virol* 9 273–280 (1982).

Extraction of HBV-DNA, PCR and Direct Sequencing 50 ul of serum were digested in the presence of 0.5% sodium dodecyl sulphate, 25 mM sodium acetate, 2.5 mM EDTA, 1 mg/ml proteinase k (Boehringer Mannheim, Lewes, UK) in a volume of 200 μl for 2 hours at 68° C., two phenolchloroform extractions were followed by two chloroform extractions and HBV-DNA was precipitated with ethanol. After washing twice with 70% ethanol, the DNA pellets were resuspended in 10 ul of water.

Five μL of the extracted HBV-DNA was used as template for PCR amplification. One set of primers (adw subtype), PO5' (5'-TGCGGGTCACCATAT, position 2818–2833) (SEQ ID NO:2), and POL3 (5'-AAGGATCCAGTTGGC, position 1409–1395) (SEQ ID NO:3) (Table 2) were used to get a 1800 bp fragment which included the pre-S1, pre-S2 and S genes (FIG. 3). Another set of primers, M3 (5'-CTGGGAGGAGTTGGGGGAGGAGATT, position 1781–1755) (SEQ ID NO:4) and 3C (5'-CTAACATTGAGATTCCCGAGA, position 2460–2439) (SEQ ID NO:5) were used to amplify the Pre-C and C regions. The same serum sample was analysed independently in China and Britain using different sets of primers.

Direct sequencing of the PCR products was carried out with the 'fmol' Sequencing Kit (Promega Co, Southampton, England). Sequencing primers (Table 1) were end-labelled with 25 μCi of $^{32}$P-adenosine triphosphase (Amersham International, Amersham, UK) in a volume of 10 μL using 10 units of polynucleotide kinase (Boehringer Mannheim) for 10 minutes at 37° C. 1.5 μL of the reaction mix was directly used in sequencing reactions. 90 μL of PCR product were precipitated with an equal volume of 4 mol/L sodium acetate and 2 volumes of isopropanol for 10 minutes at room temperature, pelleted by centrifugation for 10 minutes, and then washed two times with 70% ethanol. After resuspension in 20 μL of water, 9.5 ul of DNA was added to the reaction buffer with the end-labelled primer, and 5 units of Taq enzyme (Promega Co). Dideoxynucleotide termination sequencing was performed according to the manufacturer's instructions. Cycle sequencing was performed for 30 rounds. Denaturation, annealing and extension steps were for 30 seconds, 30 seconds and 1 minute, respectively.

Cloning and Sequencing of S Gene

Direct sequencing results showed that the first serum from patient two (February 1993) had evidence of a mixture of wild-type and mutant viruses. PCR products from this serum sample and subsequent ones from patient No. 2 were cloned into the pUC19 vector to confirm direct sequencing results. Nucleotide sequences of amplified HBV-DNA were determined with the sequenase DNA sequencing kit (Version 2.0, USB, Cambridge, England).

Hydrophobicity Plot

Amino acids 122 to 137 and 122 to 139 or 140 (including inserted amino acids) of the 'a' determinant of HBsAg from the wild type and variant viral isolates, respectively, were analysed with the Prosis software (Pharmacia, St. Albans, England).

Dot Blot Hybridisation

HBV-DNA was detectable in serum from Patient No. 1 following amplification by PCR on two separate occasions.

In Patient No. 2, this was detectable by dot blot hybridisation in March 1993 and September 1993, at 10 μg/50 μL of serum. Given that 1.0 μg of HBV-DNA is equivalent to $2.3\times10^6$ HBV genomes, it was estimated that this patient's serum contained about $4.6\times10^7$ viral particles per mL. HBsAg was detectable in the first but not the second sample. In January 1994, HBV-DNA was detectable only by PCR, and HBsAg was still undetectable.

Monoclonal Antibody Binding Studies

Binding studies in Patient No. 1 and No. 2 and an HBsAg positive patient used as a control (adw), showed that the HBsAg in the serum bound to all three monoclonal antibodies in Patient 2 and could be detected by the polyclonal anti-HBs from the AusRIA II kit (Table 2).

Sequencing of the Pre S—S Gene and Pre C/C Region

The S genes consist of 687 bp in Isolate 1, 690 in Isolate 2, respectively, and 681 bp in the wild types. The S nucleotide and amino acid sequences of the mutants were compared with a published sequence of the same subtype (adw), and also with a wild type strain from an HBeAg-positive carrier from the same region (as shown in Table 3).

Sequencing results revealed an insertion in the S gene (FIG. 4). Inserted sequences encode two additional amino acids (Arg-Ala) between codons 122 and 123 in Isolate 1, and three additional amino acids (Arg-Gly-Ala) between codons 123 and 124 in Isolate 2 (FIG. 5). These insertions occur immediately before the 'a' determinant of HBsAg. Such insertions have not been described in published sequences of known HBV subtypes and were absent from consensus sequences obtained from 30 Chinese HBsAg positive patients from the same region of China.

Direct sequencing results were verified by cloning sequencing. Of 10 clones from the first serum taken from Patient No. 2, 8 had an in-phase insertion as described above, 2 of them were wild type, whereas all 15 clones from the second and third serum samples were of the variant. Thus, the first serum from Patient No. 2 had evidence of a mixture of wild-type and mutant viruses, indicating gradual emergence of the mutant, which in subsequent sera became the predominant species. There were no previously described amino acid deletions or substitutions in the pre-S1, pre-S2 genes.

Hydrophobic Plot

This was done according to the method of Kyte and Doolittle, giving a mean hydrophobicity index of −0.48 for amino acids 122–137 of the wild type 'a' determinant −0 for amino acids 122–139 in isolate 1 and −0.89 for amino acids 122–140 in isolate 2. Thus, the mutant 'a' determinants were more hydrophobic than the same region from the wild-type virus.

REFERENCES

Ashton-Rickardt et al., *J. Med. Virol.* 29 196 (1989)
Blum et al., *J. Virol* 65 1836–42 (1991)
Botstein and Shortle, *Science* 229 1193 (1982)
Brechot et al., *N. Engl. J. Med.* 312 270–276 (1985)
Brechot et al., *J. Hepatol.* 13 (supplement) S49–55 (1991)
Brown et al., *Lancet* 2 184–187 (1984)
Carman et al., *Lancet* i 325–329 (1990)
Carman et al., *Lancet* 341 349–353 (1993)
Gregg et al., *Biotechnology* 5 479 (1987)
Harford et al., *Develop. Biol. Standard* 54 125 (1983)
Hayden and Mandecki, *DNA* 7 571 (1988)
Ho et al., *Gene* 77 51 (1989)
Lai et al., *Blood* 73 17–19 (1989)
Lai et al., *Hepatology* 12 1335–1340 (1990)
Lau et al., *Lancet* 342 1335–1340 (1993)
Liang et al., *Hepatology* 12 204–212 (1990)
Luo et al., *J. Med. Virol* 35 55–59 (1991)
McMahon et al., Cold Spring Harbor Symposium on Molecular Biology of Hepatitis B Viruses, September 1989
McMahon et al., *Hepatology* 15 757–766 (1992)
Michel et al., *Hepatology* 7(Supplement) 61–63 (1987)
Miller et al., *Hepatology* 9 322 (1989)
Miyanohara et al., *Proc. Natl. Acad. Sci. USA* 80 1 (1983)
Moriyama et al., *Lancet* 337 125 (1991)
Okamoto et al., *J. Virol.* 74 5463–67 (1987)
Okamoto et al., *Pediatric Research* 32 264–268 (1992)
Sun et al., *J. Clin. Microbiol* 26 1848–52 (1988)
Thier et al., *Lancet* ii 1273–76 (1987)
Tiollais et al., *Science* 213 406–411 (1981)
Tiollais et al., *Nature* 317 489 (1985)
Tiollais et al., *Hepatology* 7 (Supplement) 361–363 (1987)
Valenzuela et al., *Nature* 280 815 (1979)
Valenzuela et al., *Nature* 298 347 (1982)
Waters et al. *Virus Research* 22 1–12 (1991)
Waters et al., *J. Clin. Invest.* 90 2543–2547 (1992)
Weller et al., *J. Med. Virol* 9 273–280 (1982)
Zanetti et al., *Lancet*, page 1132 November 1988
Zhang et al., *Hepatology* 17 538–544 (1993)

PATENTS

European Patent No. 0226846
European Patent No. 0278940
European Patent No. 0299108
PCT Application No. 91/14703
PCT Application No. 94/26904
U.S. Pat. No. 4,649,192
U.S. Pat. No. 4,683,294
U.S. Pat. No. 4,694,074
U.S. Pat. No. 4,738,926

We claim:

1. A modified hepatitis B surface antigen protein (mHBsAg, wherein said mHBsAg has an antigenicity of HBV surface antigen (HBsAg) and wherein said mHBsAg comprises an antigenically modified envelope region in which either arginine and alanine, respectively, or arginine, glycine and alanine, respectively, are inserted between codon positions 122 and 124 of the HBsAg sequence.

2. A mHBsAg as claimed in claim 1, which is identical to wild-type HBsAg except for the insertion of arginine and alanine, respectively, between codon positions 122 and 124 of the HBsAg sequence.

3. A mHBsAg as claimed in claim 1, which is identical to wild-type HBsAg except for the insertion of arginine, glycine and alanine, respectively, between codon positions 122 and 124 of HBsAg.

4. A modified hepatitis B surface antigen protein (mHBsAg) which has the antigenicity of an HBV surface antigen (HBsAg) and is identical to wild-type HBsAg but for the insertion of at least two amino acid residues between codon positions 122 and 124 of the HBsAg sequence wherein the amino acids residues inserted are arginine and alanine in that order.

5. A mHBsAg as claimed in claim 4, wherein the amino acid residues inserted between codon positions 122 and 124 reduce the hydrophilicity of the envelope region of HBV.

6. A mHBsAg as claimed in claim 4, wherein the amino acid residues inserted codon positions 122 and 124 are arginine, glycine and alanine, in that order.

7. A mHBsAg as claimed in claim 1, wherein the mHBsAg includes Pre-S sequences.

8. A mHBsAg as claimed in claim 1, which is greater than 75% pure.

9. An expression vector comprising a DNA sequence (SEQ ID NO:6) encoding a mHBsAg according to claim 1.

10. An expression vector comprising a DNA sequence (SEQ ID NO:8) encoding a mHBsAg according to claim 1.

11. A host cell transformed with the vector of claim 9.

12. A host cell transformed with the vector of claim 10.

13. A process for preparing a mHBsAg as claimed in claim 1, said process comprising the steps of culturing a host cell in an appropriate culture medium, wherein said host cell is transformed with an expression vector, which vector contains a DNA sequence (SEQ ID NO:6) encoding said mHBsAg; and purifying the mHBsAg produced to the required degree of purity.

14. A process as claimed in claim 13, wherein the DNA sequence is SEQ ID NO:8.

15. A method for detecting mHBsAg antibodies in a test sample comprising:
a) contacting a test sample suspected of having said antibodies with the mHBsAg of claim 1, for a time and under conditions sufficient to allow antibody/antigen complexes to form; and
b) detecting the antibody/antigen complexes which contain the mHBsAg.

16. A kit for determining the presence of mHBsAg or antibody to mHBsAg, comprising a container and the mHBsAg of claim 1.

17. A kit as claimed in claim 16, wherein the mHBsAg is attached to a solid phase.

18. An immunogenic composition comprising an mHBsAg as claimed in claim 1, optionally linked to a suitable carrier or adjuvant, and a pharmaceutically acceptable excipient.

19. A method for producing antibodies to an mHBsAg comprising administering to a host the immunogenic composition as claimed in claim 18.

20. An antibody preparation comprising antibodies against mHBsAg as claimed in claim 1 for use in the diagnosis, prevention or treatment of hepatitis B infection in humans.

* * * * *

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 893 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 1:

```
GGATCCCAGA  GTCAGGGGTC  TGTATCTTCC  TGCTGGTGGC  TCCAGTTCAG  GAACAGTAAA      60
CCCTGCTCCG  AATATTGCCT  CTCACATCTC  GTCAATCTCC  GCGAGGACTG  GGGACCCCTG     120
```

-continued

```
TGACGAAC ATG GAG AAC ATC ACA TCA GGA TTC CTA GGA CCC CTG CTC GTG    170
         Met Glu Asn Ile Thr Ser Gly Phe Leu Gly Pro Leu Leu Val
          1               5                      10

TTA CAG GCG GGG TTT TTC TTG TTG ACA AGA ATC CTC ACA ATA CCG CAG    218
Leu Gln Ala Gly Phe Phe Leu Leu Thr Arg Ile Leu Thr Ile Pro Gln
 15              20                  25                      30

AGT CTA GAC TCG TGG TGG ACT TCT CTC AAT TTT CTA GGG GGA TCT CCC    266
Ser Leu Asp Ser Trp Trp Thr Ser Leu Asn Phe Leu Gly Gly Ser Pro
                 35                  40                  45

GTG TGT CTT GGC CAA AAT TCG CAG TCC CCA ACC TCC AAT CAC TCA CCA    314
Val Cys Leu Gly Gln Asn Ser Gln Ser Pro Thr Ser Asn His Ser Pro
             50                  55                  60

ACC TCC TGT CCT CCA ATT TGT CCT GGT TAT CGC TGG ATG TGT CTG CGG    362
Thr Ser Cys Pro Pro Ile Cys Pro Gly Tyr Arg Trp Met Cys Leu Arg
         65                  70                  75

CGT TTT ATC ATA TTC CTC TTC ATC CTG CTG CTA TGC CTC ATC TTC TTA    410
Arg Phe Ile Ile Phe Leu Phe Ile Leu Leu Leu Cys Leu Ile Phe Leu
     80                  85                  90

TTG GTT CTT CTG GAT TAT CAA GGT ATG TTG CCC GTT TGT CCT CTA ATT    458
Leu Val Leu Leu Asp Tyr Gln Gly Met Leu Pro Val Cys Pro Leu Ile
 95                 100                 105                 110

CCA GGA TCA ACA ACA ACC AGT ACG GGA CCA TGC AAA ACC TGC ACG ACT    506
Pro Gly Ser Thr Thr Thr Ser Thr Gly Pro Cys Lys Thr Cys Thr Thr
                 115                 120                 125

CCT GCT CAA GGC AAC TCT ATG TTT CCC TCA TGT TGC TGT ACA AAA CCT    554
Pro Ala Gln Gly Asn Ser Met Phe Pro Ser Cys Cys Cys Thr Lys Pro
             130                 135                 140

ACG GAT GGA AAT TGC ACC TGT ATT CCC ATC CCA TCG TCC TGG GCT TTC    602
Thr Asp Gly Asn Cys Thr Cys Ile Pro Ile Pro Ser Ser Trp Ala Phe
         145                 150                 155

GCA AAA TAC CTA TGG GAG TGG GCC TCA GTC CGT TTC TCT TGG CTC AGT    650
Ala Lys Tyr Leu Trp Glu Trp Ala Ser Val Arg Phe Ser Trp Leu Ser
 160                 165                 170

TTA CTA GTG CCA TTT GTT CAG TGG TTC GTA GGG CTT TCC CCC ACT GTT    698
Leu Leu Val Pro Phe Val Gln Trp Phe Val Gly Leu Ser Pro Thr Val
175                  180                 185                 190

TGG CTT TCA GCT ATA TGG ATG ATG TGG TAT TGG GGG CCA AGT CTG TAC    746
Trp Leu Ser Ala Ile Trp Met Met Trp Tyr Trp Gly Pro Ser Leu Tyr
                 195                 200                 205

AGC ATC GTG AGT CCC TTT ATA CCG CTG TTA CCA ATT TTC TTT TGT CTC    794
Ser Ile Val Ser Pro Phe Ile Pro Leu Leu Pro Ile Phe Phe Cys Leu
             210                 215                 220

TGG GTA TAC ATT TAAACCCTAA CAAAACAAAA AGATGGGGTT ATTCCCTAAA        846
Trp Val Tyr Ile
             225

CTTCATGGGC TACATAATTG GAAGTTGGGG AACTTTGCCA CAGGATC                893
```

( 2 ) INFORMATION FOR SEQ ID NO: 2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 2:

TGCGGGTCAC CATAT                                      15

( 2 ) INFORMATION FOR SEQ ID NO: 3:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 3:

```
AAGGATCCAG TTGGC                                                               15
```

( 2 ) INFORMATION FOR SEQ ID NO: 4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 4:

```
CTGGGAGGAG TTGGGGGAGG AGATT                                                    25
```

( 2 ) INFORMATION FOR SEQ ID NO: 5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 5:

```
CTAACATTGA GATTCCCGAG A                                                        21
```

( 2 ) INFORMATION FOR SEQ ID NO: 6:

( i ) SEQUENCE CHARACTERISTICS:
        ( A ) LENGTH: 687 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 6:

```
ATGGAGAACA TCACATCAGG ACTCCTAGGA CCCCTGCTCG TGTTACAGGC GGGGTTTTTC    60
TTGTTGACAA AAATCCTCAC AATACCACAG AGTCTAGACT CGTGGTGGAC TTCTCTCAAT   120
TTTCTAGGGG GAACACCCGT GTGTCTTGGC CAAAATTCGC AGTCCCAAAT CTCCAGTCAC   180
TCACCAACCT GTTGTCCTCC AATTTGTCCT GGTTATCGCT GGATGTGTCT GCGGCGTTTT   240
ATCATCTTCC TCTGCATCCT GCTGCTATGC CTCATCTTCT TGTTGGTTCT TCTGGACTAT   300
CAAGGTATGT TGCCCGTTTG TCCTCTAATT CCAGGATCAT CAACAACCAG CACCGGACCA   360
TGCAAACGGG CAACCTGCAC AACTCCTGCT CAAGGAACCT CTATGTTTCC CTCATGTTGC   420
TGTACAAAAC CTACGGACGG AAACTGCACC TGTATTCCCA TCCCATCATC TTGGCGTTTC   480
GCAAAATACC TATGGGAGTG GGCCTCAGTC CGTTTCTCTT GGCTCAGTTT ACTAGTGCCA   540
TTTGTTCAGT GGTTCGTAGG GCTTTCCCCC ACTGTCTGGC TTTCAGTTAT ATGGATGATG   600
TGGTTTTGGG GGCCAAGTCT GATCAACATC TTGAGTCCCT TTATGCCGCT GTTACCAATT   660
TTCTTTTGTC TTTGGGTATA CATTTAA                                       687
```

( 2 ) INFORMATION FOR SEQ ID NO: 7:

( i ) SEQUENCE CHARACTERISTICS:
        ( A ) LENGTH: 681 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 7:

```
ATGGAGAACA  TCGCATCAGG  ACTCCTAGGA  CCCCTGCTCG  TGTTACAGGC  GGGGTTTTTC    60
TTGTTGACAA  AAATCCTCAC  AATACCACAG  AGTCTAGACT  CGTGGTGGAC  TTCTCTCAAT   120
TTTCTAGGGG  GAACACCCGT  GTGTCTTGGC  CAAAATTCGC  AGTCCCAAAT  CTCCAGTCAC   180
TCACCAACTT  GTTGTCCTCC  GATTTGTCCT  GGTTATCGCT  GGATGTGTCT  GCGGCGTTTT   240
ATCATCTTCC  TCTGCATCCT  GCTGCTATGC  CTCATCTTCT  TGTTGGTTCT  TCTGGACTAT   300
CAAGGTATGT  TGCCCGTTTG  TCCTCTAATT  CCAGGATCAT  CAACCACCAG  CACCGGACCA   360
TGCAAAACCT  GCACGACTCC  TGCTCAAGGA  ACCTCTATGT  TTCCCTCATG  TTGCTGTACA   420
AAACCTACGG  ACGGAAACTG  CACCTGTATT  CCCATCCCAT  CATCTTGGGC  TTTCGCAAAA   480
TACCTATGGG  AGTGGGCCTC  AGTCCGTTTC  TCTTGGCTCA  GTTACTAGT   GCCATTTGTT   540
CAGTGGTTCG  TAGGGCTTTC  CCCCACTGTC  TGGCTTTCAG  TTATATGGAT  GATGTGGTTT   600
TGGGGGCCAA  GTCTGTACAA  CATCTTGAGT  CCCTTTATGC  CGCTGTTACC  AATTTTCTTT   660
TGTCTTTGGG  TATACATTTA  A                                                681
```

( 2 ) INFORMATION FOR SEQ ID NO: 8:

( i ) SEQUENCE CHARACTERISTICS:
        ( A ) LENGTH: 690 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 8:

```
ATGGAGAACA  TCACATCAGG  ACTCCTAGGA  CCCCTGCTCG  TGTTACAGGC  GGGGTTTTTC    60
TTGTTGACAA  AAATCCTCAC  AATACCACAG  AGTCTAGACT  CGTGGTGGAC  TTCTCTCAAT   120
TTTCTAGGGG  GAACACCCGT  GTGTCTTGGC  CAAAATTCGC  AGTCCCAAAT  CTCCAGTCAC   180
TCACCAACCT  GTTGTCCTCC  AATTTGTCCT  GGTTATCGCT  GGATGTGTCT  GCGGCGTTTT   240
ATCATCTTCC  TCTGCATCCT  GCTGCTATGC  CTCATCTTCT  TGTTGGTTCT  TCTGGACTAT   300
CAAGGTATGT  TGCCCGTTTG  TCCTCTAATT  CCAGGATCAT  CAACAACCAG  CACCGGACCA   360
TGCAAAACAC  GGGGCGCCTG  CACAACTCCT  GCTCAAGGAA  CCTCTATGTT  TCCCTCATGT   420
TGCTGTACAA  AACCTACGGA  CGGAAACTGC  ACCTGTATTC  CCATCCATC   ATCTTGGGCT   480
TTCGCAAAAT  ACCTATGGGA  GTGGGCCTCA  GTCCGTTTCT  CTTGGCTCAG  TTTACTAGTG   540
CCATTTGTTC  AGTGGTTCGT  AGGGCTTTCC  CCCACTGTCT  GGCTTTCAGT  TATATGGATG   600
ATGTGGTTTT  GGGGGCCAAG  TCTGTACAAC  ATCTTGAGTC  CCTTTATGCC  GCTGTTACCA   660
ATTTTCTTTT  GTCTTTGGGT  ATACATTTAA                                       690
```

( 2 ) INFORMATION FOR SEQ ID NO: 9:

( i ) SEQUENCE CHARACTERISTICS:
        ( A ) LENGTH: 681 base pairs
        ( B ) TYPE: nucleic acid
        ( C ) STRANDEDNESS: single (D) TOPOLOGY: linear (i i) MOLECULE TYPE: DNA (genomic)

(x i) SEQUENCE DESCRIPTION: SEQ ID NO: 9:

| | | | | | | |
|---|---|---|---|---|---|---|
| ATGGAGAACA | TCGCATCAGG | ACTCCTAGGA | CCCCTGCTCG | TGTTACAGGC | GGGGTTTTTC | 60 |
| TTGTTGACAA | AAATCCTCAC | AATACCACAG | AGTCTAGACT | CGTGGTGGAC | TTCTCTCAAT | 120 |
| TTTCTAGGGG | GAACACCCGT | GTGTCTTGGC | CAAAATTCGC | AGTCCCAAAT | CTCCAGTCAC | 180 |
| TCACCAACTT | GTTGTCCTCC | GATTTGTCCT | GGTTATCGCT | GGATGTGTCT | GCGGCGTTTT | 240 |
| ATCATCTTCC | TCTGCATCCT | GCTGCTATGC | CTCATCTTCT | TGTTGGTTCT | TCTGGACTAT | 300 |
| CAAGGTATGT | TGCCCGTTTG | TCCTCTAATT | CCAGGATCAT | CAACCACCAG | CACCGGACCA | 360 |
| TGCAAAACCT | GCACGACTCC | TGCTCAAGGA | ACCTCTATGT | TTCCCTCATG | TTGCTGTACA | 420 |
| AAACCTACGG | ACGGAAACTG | CACCTGTATT | CCCATCCCAT | CATCTTGGGC | TTTCGCAAAA | 480 |
| TACCTATGGG | AGTGGGCCTC | AGTCCGTTTC | TCTTGGCTCA | GTTACTAGT | GCCATTGTT | 540 |
| CAGTGGTTCG | TAGGGCTTTC | CCCCACTGTC | TGGCTTTCAG | TTATATGGAT | GATGTGGTTT | 600 |
| TGGGGGCCAA | GTCTGTACAA | CATCTTGAGT | CCCTTTATGC | CGCTGTTACC | AATTTTCTTT | 660 |
| TGTCTTTGGG | TATACATTTA | A | | | | 681 |

(2) INFORMATION FOR SEQ ID NO: 10:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO: 10:

| | | |
|---|---|---|
| TGCGGGTCAC | CATAT | 15 |

(2) INFORMATION FOR SEQ ID NO: 11:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO: 11:

| | | |
|---|---|---|
| CAATCGGCAG | TCAGG | 15 |

(2) INFORMATION FOR SEQ ID NO: 12:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO: 12:

| | | |
|---|---|---|
| AGGCATAGCA | GCAGG | 15 |

(2) INFORMATION FOR SEQ ID NO: 13:

(i) SEQUENCE CHARACTERISTICS:
  (A) LENGTH: 20 base pairs

-continued (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 13:

GGCACTAGTA AACTGAGCCA 20

(2) INFORMATION FOR SEQ ID NO: 14:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 14:

GCAAAGTTCC CCAACTTC 18

(2) INFORMATION FOR SEQ ID NO: 15:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 15:

AAGGATCCAG TTGGC 15